US006953873B2

(12) United States Patent
Cortright et al.

(10) Patent No.: US 6,953,873 B2
(45) Date of Patent: Oct. 11, 2005

(54) LOW-TEMPERATURE HYDROCARBON PRODUCTION FROM OXYGENATED HYDROCARBONS

(75) Inventors: Randy D. Cortright, Madison, WI (US); James A. Dumesic, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/435,208

(22) Filed: May 9, 2003

(65) Prior Publication Data

US 2003/0220531 A1 Nov. 27, 2003

Related U.S. Application Data

(60) Provisional application No. 60/379,486, filed on May 10, 2002.

(51) Int. Cl.$^7$ .............................................. C07C 1/207

(52) U.S. Cl. ...................... 585/733; 585/357; 585/469; 585/638; 585/639; 585/640

(58) Field of Search ................................ 595/357, 469, 595/638, 639, 640, 733

(56) References Cited

U.S. PATENT DOCUMENTS

| | | | |
|---|---|---|---|
| 4,223,001 A | 9/1980 | Novotny et al. | |
| 4,300,009 A | 11/1981 | Haag et al. | |
| 4,433,184 A | * 2/1984 | Huibers et al. ............. | 568/863 |
| 4,503,278 A | 3/1985 | Chen et al. | |
| 4,549,031 A | 10/1985 | Chen et al. | |
| 4,554,260 A | 11/1985 | Pieters et al. | |
| 5,019,135 A | 5/1991 | Sealock, Jr. et al. | |
| 5,516,960 A | 5/1996 | Robinson | |
| 5,616,154 A | 4/1997 | Elliott et al. | |
| 5,630,854 A | 5/1997 | Sealock, Jr. et al. | |
| 5,651,953 A | 7/1997 | Yokoyama et al. | |
| 5,814,112 A | 9/1998 | Elliott et al. | |
| 5,861,137 A | 1/1999 | Edlund | |
| 6,059,995 A | 5/2000 | Topsoe et al. | |
| 6,171,992 B1 | 1/2001 | Autenrieth et al. | |
| 6,207,132 B1 | 3/2001 | Lin et al. | |
| 6,221,117 B1 | 4/2001 | Edlund et al. | |
| 6,235,797 B1 | 5/2001 | Elliot et al. | |
| 6,280,701 B1 | 8/2001 | Autenrieth et al. | |
| 6,361,757 B1 | 3/2002 | Shikada et al. | |
| 6,387,554 B1 | 5/2002 | Verykios | |
| 6,413,449 B1 | 7/2002 | Weiland et al. | |
| 6,607,707 B2 | 8/2003 | Reichman et al. | |
| 6,623,719 B2 | 9/2003 | Lomax, Jr. et al. | |
| 6,699,457 B2 | 3/2004 | Cortright et al. | |
| 6,749,828 B1 | 6/2004 | Fukunaga | |

FOREIGN PATENT DOCUMENTS

WO    WO 99/48804 A1    9/1999

OTHER PUBLICATIONS

Brown et al, Carbon–Halogen Bond Scission and Rearrangement of β–Halohydrins on the Rh(111) Surface, *J. Phys. Chem.*, 98:12737–12745 (1994).
Kawai et al., Production of Hydrogen and Hyrdocarbon From Cellulose and Wate.; Chemistry Letters, pp. 1185–1188 (1981).
Minowa et al., Hydrogen Production from Wet Cellulose by Low Temperature Gasification Using a Reduced Nickel Catalyst, *Chemistry Letters*, pp. 937–938 (1995).
Minowa et al., Hydrogen Production from Cellulose in Hot compressed Water Using Reduced Nickel Catalyst: Product Distribution at Different Reaction Temperatures, *Journal of Chemical Engineering of Japan*, vol. 1, No. 3, pp. 488–491 (1998).
J. Rostrup–Noelsen, Conversion of hydrocarbons and alcohols for fuel cells, *Phys. Chem. Chem. Phys.* 3, 283 (2001).
Usui et al., Selective Hydrogen Production from Cellulose at Low Temperature Catalyzed by Supported Group 10 Metal, *Chemistry Letters*, pp. 1166–1167 (2000).
Wang et al., Catalytic steam reforming of biomass–derived oxygenates: acetic acid and hydroxyavetaldehyde, *Applied Catalysis A: General* 143, 245–270 (1996).
Bardin et al. (1998) "Acidity of Keggin–type Heteropolycompounds Evaluated by Catalytic Probe Reactions, Sorption Microcalorimetry and Density Functional Quantum Chemical Calculations," *J. of Physical Chemistry B*, 102:10817–10825.
Chen et al. (Aug. 1986) "Liquid Fuel from Carbohydrates," *Chemtech* 506–509.
Elliott et al. (1999) "Chemical Processing in High–Pressure Aqueous Environments, 6, Demonstration of Catalytic Gasification for Chemical Manufacturing Wastewater Cleanup in Industrial Plant," *Ind. Eng. Chem. Res.* 38:879–883.
Nelson et al. (1984) "Application of Direct Thermal Liquefaction for the Conversion of Cellulosic Biomass," *Ind. Eng. Chem. Prod. Res. Dev.* 23(3):471–475.
Yoshida et al. (201) "Gasification of Cellulose, Xylan, and Lignin Mixtures in Supercritical Water," Ind. Eng. Chem. Res. 40:5469–5474.

* cited by examiner

Primary Examiner—Thuan D Dang
(74) Attorney, Agent, or Firm—Joseph T. Leone, Esq.; DeWitt Ross & Stevens S.C.

(57) ABSTRACT

Disclosed is a method of producing hydrocarbons from oxygenated hydrocarbon reactants, such as glycerol, glucose, or sorbitol. The method can take place in the vapor phase or in the condensed liquid phase (preferably in the condensed liquid phase). The method includes the steps of reacting water and a water-soluble oxygenated hydrocarbon having at least two carbon atoms, in the presence of a metal-containing catalyst. The catalyst contains a metal selected from the group consisting of Group VIIIB transitional metals, alloys thereof, and mixtures thereof. These metals are supported on supports that exhibit acidity or the reaction is conducted under liquid-phase conditions at acidic pHs. The disclosed method allows the production of hydrocarbon by the liquid-phase reaction of water with biomass-derived oxygenated compounds.

50 Claims, 8 Drawing Sheets

LOW-TEMPERATURE HYDROCARBON PRODUCTION FROM OXYGENATED HYDROCARBONS

CROSS-REFERENCE TO RELATED APPLICATIONS

Priority is hereby claimed to provisional application Ser. No. 60/379,486, filed May 10, 2002, and incorporated herein.

FEDERAL FUNDING STATEMENT

This invention was made with United States government support awarded by NSF Grant No. 9802238 and DOE Grant No. DE-FG02-84ER13183. The United States has certain rights in this invention.

FIELD OF THE INVENTION

The invention is directed to a method of producing hydrocarbons by low-temperature vapor- and condensed liquid-phase reforming of oxygenated hydrocarbons.

BACKGROUND OF THE INVENTION

Hydrocarbons feedstocks are currently extracted from the ground and combusted to generate energy. These hydrocarbon feedstocks currently are favored as they are easily transported as liquid (i.e. gasoline). These non-renewable feedstocks will eventually be depleted over time. Furthermore, when combusted these materials create carbon dioxide, a greenhouse gas that may contribute to global warming. A key challenge for promoting and sustaining the vitality and growth of the energy industry (as well as the entire industrial sector of society) is to develop efficient and environmentally benign technologies for generating fuel, such as combustible hydrocarbons, from renewable resources. Notably, if hydrocarbon fuel for consumption in fuel cells (and other types of equipment) can be generated efficiently from renewable sources, then non-renewable resources such as petroleum feedstocks can be used for other, more beneficial, and less environmentally deleterious purposes. Moreover, the generation of energy from renewable resources such as biomass, reduces the net rate of production of carbon dioxide, an important greenhouse gas that contributes to global warming. This is because the biomass itself, i.e., plant material, consumes carbon dioxide during its life cycle.

A series of patents to Elliott et al. and assigned to Battelle Memorial Institute describe the production of a "product gas" (primarily methane, carbon dioxide, and hydrogen) from liquid organic material, using a metal catalyst. Specifically, U.S. Pat. No. 5,616,154 describes a process wherein the liquid organic material and water are reacted in a pressure vessel at a temperature of from about 300° C. to about 450° C., and at a pressure of at least 130 atm (1,911 psi). The catalyst used in the process is a reduced form of ruthenium, rhodium, osmium, or iridium. The liquid organic material used as a feedstock is defined as "any organic compound or mixture of such compounds that exists as or decomposes to a liquid or a gas at a temperature of at least 250° C. and at a pressure of 50 atm or more." The process is aimed at both the production of energy and the destruction of liquid waste streams, such as hexamethylene diamine in water (a by-product from the production of nylon 6,6).

U.S. Pat. No. 5,814,112 (to Elliott et al. and a continuation-in-part of the patent described in the previous paragraph) describes a nickel/ruthenium catalyst for steam reforming and hydrogenation reactions. U.S. Pat. No. 6,235,797, also to Elliott et al., describes a ruthenium catalyst that is essentially free or nickel and rhenium and which is adhered to a titania support, wherein the titania is greater than 75% rutile. The catalyst is specifically designed for use in the aqueous-phase hydrogenation of organic compounds.

In similar fashion, U.S. Pat. No. 5,630,854, issued to Sealock et al. and assigned to Battelle Memorial Institute, describes a method of converting waste organic materials into a product gas. In this method, the stream of organic waste is reacted in a pressure vessel that has been purged of oxygen. The reaction takes place at elevated temperatures and at a pressure of at least 50 atm (735 psi), in the presence of a reduced nickel catalyst.

U.S. Pat. No. 4,300,009, to Haag et al., describes a process for manufacturing liquid hydrocarbons. In this process, organic plant material having a hydrogen-to-carbon ratio of from about 1 to 1, to about 2.2 to 1, is contacted at elevated temperature and pressure with a crystalline aluminosilicate zeolite having a pore diameter great than about 5 Å. According to the specification, at least 50% of the liquid hydrocarbons so produced distill at a temperature below about 170° C.

U.S. Pat. Nos. 4,503,278 and 4,549,031, both issued to Chen & Koenig, describe a method for converting carbohydrates to hydrocarbons. In this process, aqueous solutions of the carbohydrate are contacted with a particular type of crystalline silicate zeolite catalyst at elevated temperatures and at pressures ranging from 1 to 50 atm, thereby yielding hydrocarbon products. A similar approach is described in a paper authored by Chen, Koenig and Degnan Jr. (August 1986) "Liquid Fuel from Carbohydrates," *Chemtech* 506–509.

U.S. Pat. No. 5,516,960, to Robinson, describes a method for producing hydrocarbon fuels wherein polyhydric alcohols, cellulose, or hemicellulose are reacted to yield hydrocarbons. In this reaction, when using cellulose or hemicellulose as the feedstock, the cellulose or hemicellulose is first depolymerized to sorbitol or xylitol, respectively. This is accomplished using well known reductive depolymerization chemistry. The sorbitol or xylitol is then converted to iodoalkanes by a reacting the sorbitol/xylitol with hydroiodic acid and a liquid-phase, phosphorous-containing reducing agent. This reaction yields primarily 2-iodohexane in the case of sorbitol and 2-iodopentane in the case of xylitol. The reaction takes place in boiling aqueous solution at atmospheric pressure. The iodoalkanes so formed may then be de-halogenated to yield alkenes, and then reduced to yield alkanes.

Yoshida & Matsumura (2001) "Gasification of Cellulose, Xylan, and Lignin Mixtures in Supercritical Water," Ind. Eng. Chem. Res. 40:5469–5474, describe reacting cellulose, xylan, and lignin mixtures in supercritical water in the presence of a nickel catalyst. The reactions were carried in a sealed vessel purged of oxygen, at a temperature of 400° C., and at a pressure of from 26 to 29 MPa (3,770 to 4,205 psi).

Elliott et al. (1999) "Chemical Processing in High-Pressure Aqueous Environments. 6. Demonstration of Catalytic Gasification for Chemical Manufacturing Wastewater Cleanup in Industrial Plant," *Ind. Eng Chem.* Res. 38:879–883, describes the high-pressure (~20 MPa) catalytic gasification of organic compounds as a possible route for purifying wastewaters generated at chemical manufacturing plants. The equipment used was a fixed-bed, tubular reactor and was operated at 20 MPa and 350° C.

Nelson et al. (1984) "Application of Direct Thermal Liquefaction for the Conversion of Cellulosic Biomass," *Ind. Eng. Chem. Prod. Res. Dev.* 23(3):471–475, describes the chemical conversion of pure cellulose into a mixture of phenol, cyclopentanones, and hydroquinones. The conversion was accomplished by charging an autoclave with cellulose, water, and anhydrous sodium carbonate. The autoclave was then purged of air. The reaction was then initiated at temperatures of from 250° C. to 400° C., at pressures ranging from roughly 10.3 MPa (1,494 psi) to 20.7 MPa (3,000 psi).

Thus, there remains a long-felt and unmet need to develop methods for producing hydrocarbons from renewable resources such as biomass. Such methods would convert either low value waste biomass such as sawdust and cheese whey or biomass created for energy production such as switchgrass to hydrocarbons. The combustion of the resulting hydrocarbons would not add to the net production of carbon dioxide (a greenhouse gas) as the resulting carbon dioxide will be refix through biomass growth. The resulting hydrocarbon would have a low sulfur content, would be renewable, and derived from non-flammable starting materials. Moreover, to maximize energy output, there remains an acute need to develop a method for producing hydrocarbons that proceeds at a significantly lower temperature than catalytic cracking of hydrocarbons derived from petroleum feedstocks. Lastly, there remains a long-felt and unmet need to simplify the reforming process by developing a method for producing hydrocarbons that can be performed in a single reactor.

SUMMARY OF THE INVENTION

The invention is directed to a method of producing hydrocarbons via the reforming of an oxygenated hydrocarbon feedstock. The method comprises reacting water and a water-soluble oxygenated hydrocarbon having at least two carbon atoms, in the presence of a metal-containing catalyst. The catalyst comprises a metal selected from the group consisting of Group VIII transitional metals, alloys thereof, and mixtures thereof. The method can be optimized to yield predominately n-alkanes, principally $C_2$ to $C_6$ n-alkanes (i.e., ethane, propane, butane, pentane, and hexane), or to yield a product mixture enriched in smaller alkanes, such as propane and ethane.

It is generally preferred that the water and the oxygenated hydrocarbon are reacted at a temperature of from about 100° C. to about 450° C., and more preferably from about 100° C. to about 300° C. and at a pressure where the water and the oxygenated hydrocarbon remain condensed liquids. It is preferred that the water and the oxygenated hydrocarbon are reacted at a pressure greater than the vapor pressure of water at the reaction temperature (generally less than about 500 psig, although higher pressures are acceptable).

It is preferred that the water and the oxygenated hydrocarbon are reacted at a pH of from about 1.0 to about 8.0.

It is preferred that the catalyst comprise a metal selected from the group consisting of nickel, palladium, platinum, ruthenium, rhodium, iridium, cobalt, iron, osmium alloys thereof, and mixtures thereof. Optionally, the catalyst may also be further alloyed or mixed with a metal selected from the group consisting of Group IB metals, Group IIB metals, and Group VIIb metals, and from among these, preferably copper, zinc, and/or rhenium. It is also much preferred that the catalyst be adhered to a support, such as silica, alumina, zirconia, titania, ceria, vanadia, carbon, heteropolyacids, silica-alumina, silica nitride, boron nitride, and mixtures thereof. Furthermore, the active metals may be adhered to a nanoporous support, such as zeolites, nanoporous carbon, nanotubes, and fullerenes.

The support itself may be surface-modified to modify surface moieties, especially surface hydrogen and hydroxyl moieties that may cause localized pH fluctuations. The support can be surface-modified by treating it with silanes, alkali compounds, alkali earth compounds, and the like.

The method can also further comprise reacting the water and the water-soluble oxygenated hydrocarbon in the presence of a water-soluble acids such as hydrochloric acid, nitric acid, phosphoric acid, and organic acids. Hydrochloric acid (HCl) is preferred.

It is much preferred that the water-soluble oxygenated hydrocarbon has a carbon-to-oxygen ratio of 1:1. Particularly preferred oxygenated hydrocarbons include ethanediol, ethanedione, glycerol, glyceraldehyde, aldotetroses, aldopentoses, aldohexoses, ketotetroses, ketopentoses, ketohexoses, and alditols. From among the oxygenated hydrocarbons having six carbon atoms, glucose and sorbitol are preferred. Ethanediol, glycerol, and glyceraldehyde are the preferred oxygenated hydrocarbons from among those having less than six carbon atoms.

The invention will also function with mixed feedstocks of oxygenated hydrocarbons, that is, feedstocks containing mixtures of two or more oxygenated hydrocarbons.

The present invention thus provides methods for producing hydrocarbons via a low-temperature, catalytic reforming of oxygenated hydrocarbon compounds such as ethanediol, glycerol, sorbitol, glucose, and other water-soluble carbohydrates. For the purpose of the present invention, "reforming" or "steam reforming" is defined as the reaction of an oxygenated hydrocarbon feedstock to yield hydrocarbons and/or hydrogen and carbon dioxide.

A principal advantage of the subject invention is that the oxygenated hydrocarbon reactants can be produced from renewable resources, such as biomass. Thus, the present method can be used to generate a fuel source, namely hydrocarbons, from an abundant and fully renewable source. Also, because living plant matter consumes carbon dioxide, the use of these feedstocks in power generation applications does not result in a net increase of carbon dioxide vented to the atmosphere.

Another equally important advantage of the present method is that it functions at temperatures (100° C. to 400° C.) that allow for the conversion of the water-soluble oxygenated compounds in the condensed liquid phase.

Another beneficial aspect of the present invention is that it allows for the reforming of the oxygenated hydrocarbon and a simultaneous WGS reaction to take place in a single reactor. Accordingly, the primary products are hydrocarbons, hydrogen, and carbon dioxide, and the formation of hazardous carbon monoxide is minimized.

Still another advantage of the present invention is that when the method is carried out in the condensed liquid phase, it eliminates the need to vaporize water to steam. This is a critical concern in large-scale operations due to the high energy costs required to vaporize large amounts of water. The heat of vaporization of water is more than 2000 kJ per kilogram. By eliminating the need to vaporize the water, the amount of energy that must be input into the claimed method to yield hydrocarbons is greatly reduced. The overall energy yield, therefore, is concomitantly increased.

Thus, the subject method provides a means to convert oxygenated hydrocarbons to yield hydrocarbons, using a single reactor bed and reactor chamber, and at low temperatures. Such a reactor system can be fabricated at a reduced volume and can be used to produce hydrocarbons that are substantially free of contaminates for use in portable fuel cells or for use in applications in remote locations. The method can also be optimized to yield a product mixture tending to contain large amounts of butane, pentane, and hexane, products that can easily be separated from the aqueous reaction mixture (as compared to products such as ethanol, which forms an azeotrope with water).

Another advantage of the present invention is that it can be selectively optimized to yield hydrocarbons having 4 or more carbon atoms, such as butane, pentane, and hexane, or it can be selectively optimized to yield smaller-chain hydrocarbons such as ethane and propane. The hydrocarbon stream so produced can then be further manipulated, if desired. For example, the hydrocarbons can be dehydrogenated to yield olefins.

The process will work with literally any water-soluble carbohydrate, including glycerol, sorbitol, glucose, sucrose, lactose, xylose, etc. Disaccharides are particularly preferred.

The hydrocarbons produced using the present invention can be utilized in any process where a hydrocarbon is required. Thus, the hydrocarbons can be used as conventional fuel or, for example, as a fuel for solid oxide fuel cells. The method yields a low sulfur content hydrocarbon stream. When low sulfur content reactants are utilized, the method yields a hydrocarbon stream that is substantially free of both sulfur and carbon monoxide. This type of hydrocarbon stream is highly suitable for use in fuel cells, where sulfur and/or carbon monoxide can poison the catalysts located at the electrodes of each fuel cell.

DETAILED DESCRIPTION OF THE INVENTION

The present invention is an energy efficient method for reforming oxygenated hydrocarbons with water at low temperatures and in the liquid-phase. As used herein to describe the present invention, the terms "reforming," "steam reforming," and "steam reformation"are synonymous. These terms shall generically denote the overall reaction of an oxygenated hydrocarbon and water to yield a product mixture comprising hydrocarbons and/or hydrogen and $CO_2$, regardless of whether the reaction takes place in the gaseous phase or in the condensed liquid phase. Where the distinction is important, it shall be so noted.

When the steam reforming of oxygenated hydrocarbons is carried out in the liquid phase, the present invention makes it possible to produce hydrocarbons from aqueous solutions of oxygenated hydrocarbons having limited volatility, such as glucose and sorbitol.

Abbreviations and Definitions:

"GC"=gas chromatograph or gas chromatography.

"GHSV"=gas hourly space velocity.

"Heteropolyacid"=a class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net (−3) charge, and thus requires 3 cations to satisfy electroneutrality. If the cations are protons, the material functions as a Brønsted acid. The acidity of these compounds (as well as other physical characteristics) can "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817–10825.

"psig"=pounds per square inch relative to atmospheric pressure (i.e., gauge pressure).

"Space Velocity"=the mass/volume of reactant per unit of catalyst per unit of time.

"TOF"=turnover frequency.

"WHSV"=weight hourly space velocity=mass of oxygenated compound per mass of catalyst per h.

"WGS"=water-gas shift.

Thermodynamic Considerations:

The stoichiometric reaction for generating hydrogen by the reaction of water with an oxygenated hydrocarbon having a carbon-to-oxygen ration of 1:1 is given by reaction (1):

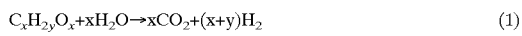

$$C_xH_{2y}O_x+xH_2O \rightarrow xCO_2+(x+y)H_2 \tag{1}$$

Figure 1:
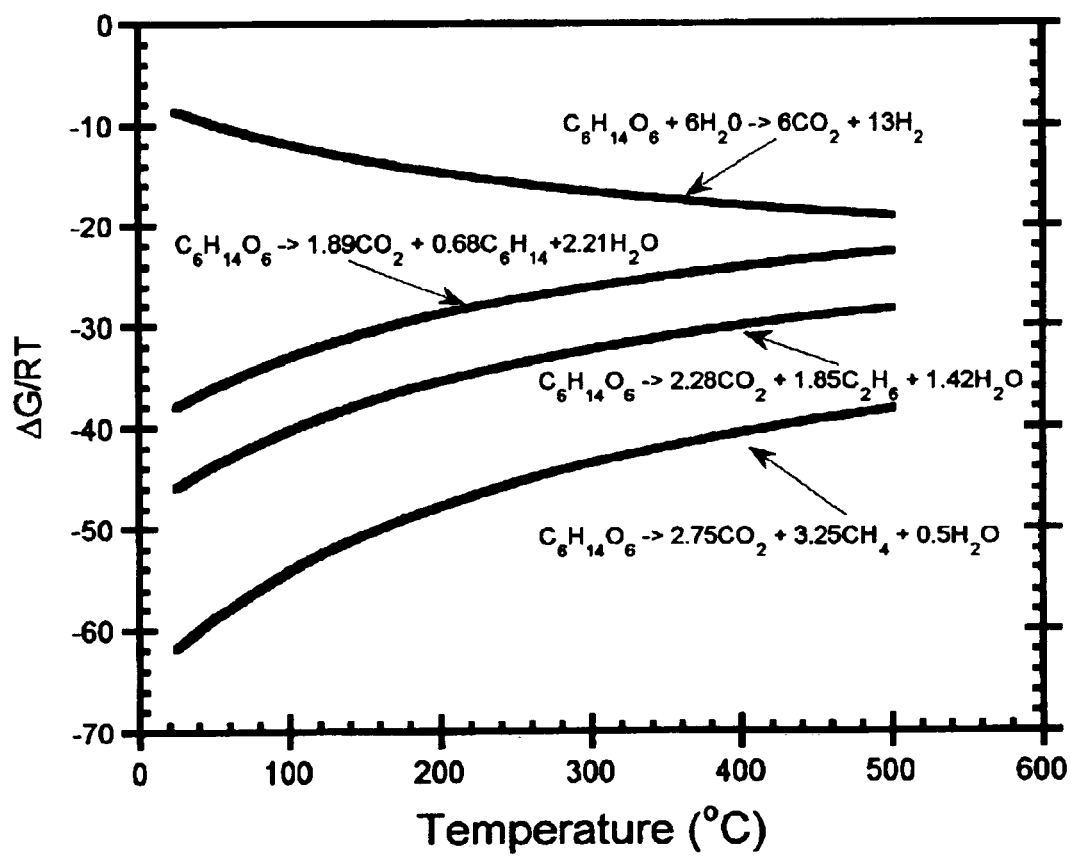
FIG. 1 is a graph depicting the temperature versus $\Delta G°/RT$ for the conversion of sorbitol to hydrogen, carbon dioxide, water, and various hydrocarbons. Note that these reactions are thermodynamically favored (i.e., $\Delta G°/RT<0$) across the entire temperature range presented in the graph.

FIG. 1 is a graph depicting the changes in the standard Gibbs free energy ($\Delta G°$) associated with reaction (1) for sorbitiol ($C_6H_{14}O_6$). The values plotted in FIG. 1 have been normalized per mole of $CO_2$. The $\Delta G°$ data points shown in FIG. 1 have been divided by RT. FIG. 1 is therefore a plot having $\Delta G°/RT$ on the Y-axis and temperature (in ° C.) on the X-axis. It can be seen from FIG. 1 that the generation of hydrogen and $CO_2$ is thermodynamically favorable (i.e., $\Delta G°$ is negative) at temperatures between 25 and 500° C.

Similarly, the reforming reaction can be optimized not to yield hydrogen, but to yield hydrocarbons. As FIG. 1. shows, from a thermodynamic standpoint, the more favored reaction yields a mixture of water, $CO_2$ and hydrocarbons:

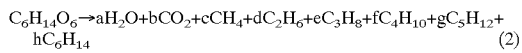

$$C_6H_{14}O_6 \rightarrow aH_2O+bCO_2+cCH_4+dC_2H_6+eC_3H_8+fC_4H_{10}+gC_5H_{12}+hC_6H_{14} \tag{2}$$

Still referring to FIG. 1, the individual reactions for the production of methane, ethane, and hexane are all thermodynamically favored (i.e., $\Delta G°/RT<0$) across the entire temperature range presented in the graph. Moreover, the production of these hydrocarbons is more favorable compared to the generation of hydrogen from the reaction of water with sorbitol. The thermodynamics for the formation of propane, butane, and pentane fit smoothly within the homologous series (between ethane and hexane), but these traces have been omitted from FIG. 1 for clarity. Thus, as described in full below, the present reaction can be optimized to yield a product mixture comprising almost exclusively hydrocarbons rather than hydrogen.

Figure 2:
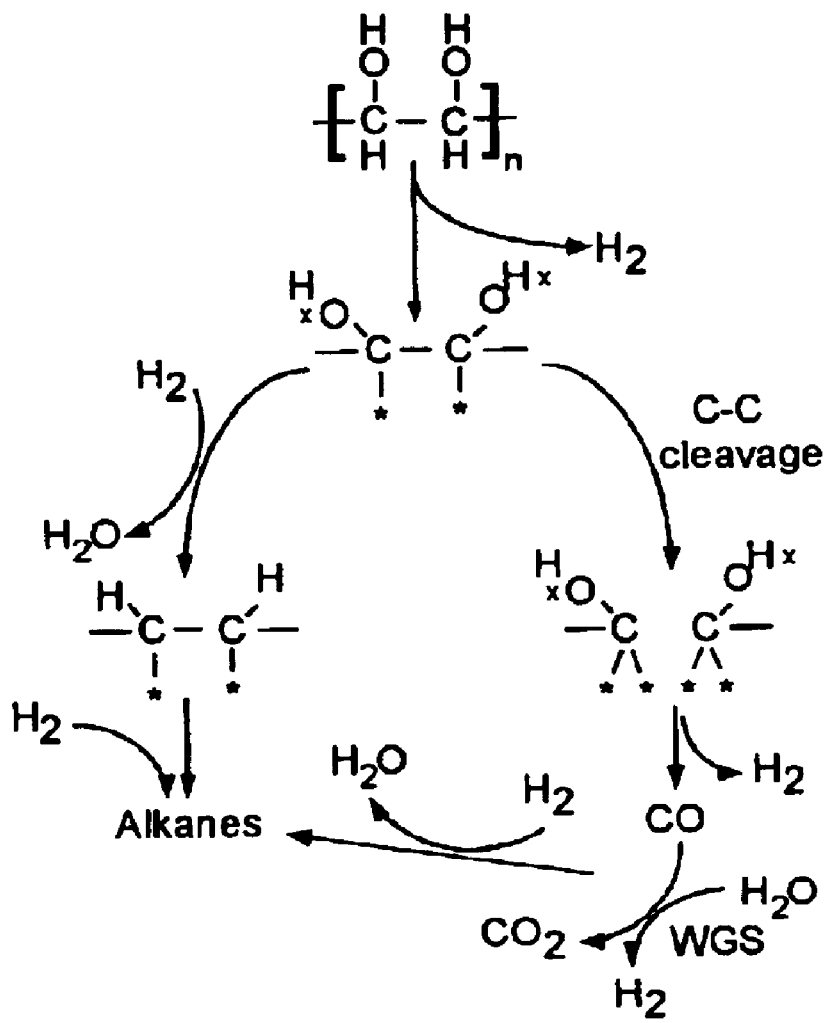
FIG. 2 presents reaction pathways for production of $H_2$ and alkanes from reactions of carbohydrates with water on metal catalysts (x=1 and x=0 correspond to C—OH and C═O groups, respectively; * represents a surface metal site).

FIG. 2 shows a schematic representation of reaction pathways that are suggested to be involved in the formation of $H_2$ and alkanes from oxygenated hydrocarbons (shown as carbohydrates) over a metal catalyst. The carbohydrate first undergoes dehydrogenation steps to give adsorbed intermediates, prior to cleavage of C—C or C—O bonds. Subsequent cleavage of C—C bonds leads to the formation of CO and $H_2$, and CO reacts with water to form $CO_2$ and $H_2$ by the water-gas shift. The further reaction of CO and/or $CO_2$ with $H_2$ leads to alkanes and water by methanation and Fischer-Tropsch reactions. The methanation and Fischer-Tropsch reactions are metal-catalyzed reaction that can generate hydrocarbon with one or more carbon. Typical metals that catalyze the methanation and Fischer-Tropsch reaction are ruthenium, cobalt, nickel, and iron. In addition, it is possible to form alkanes on the metal catalyst by first cleaving C—O bonds in adsorbed carbohydrate intermediates, followed by the hydrogenation of the resulting adsorbed $C_nH_x$ species.

In addition to the pathways in FIG. 2 that take place on metal surfaces, reactions may also take place on the surface of the catalyst support and/or in the solution phase, and these reactions can lead to further variations in the selectivities for production of $H_2$ and alkanes. These reactions convert oxygenated compounds, in which each carbon atoms is bonded to an oxygen atom, to organic acids. In general, these reactions involve dehydrogenation and subsequent rearrangement steps that form carbon atoms that are not bonded to oxygen atoms, and these carbon atoms will be subsequently converted to alkane moieties. Oxygenated compounds can also undergo dehydration reactions on acidic catalyst supports (e.g., on supports having low isoelectric points), followed by hydrogenation reactions on metallic catalyst surfaces in the presence of $H_2$, again leading to carbon atoms that are not bonded to oxygen atoms. This bi-functional dehydration/hydrogenation pathway consumes $H_2$ and leads to the subsequent formation of alkanes.

Figure 3:
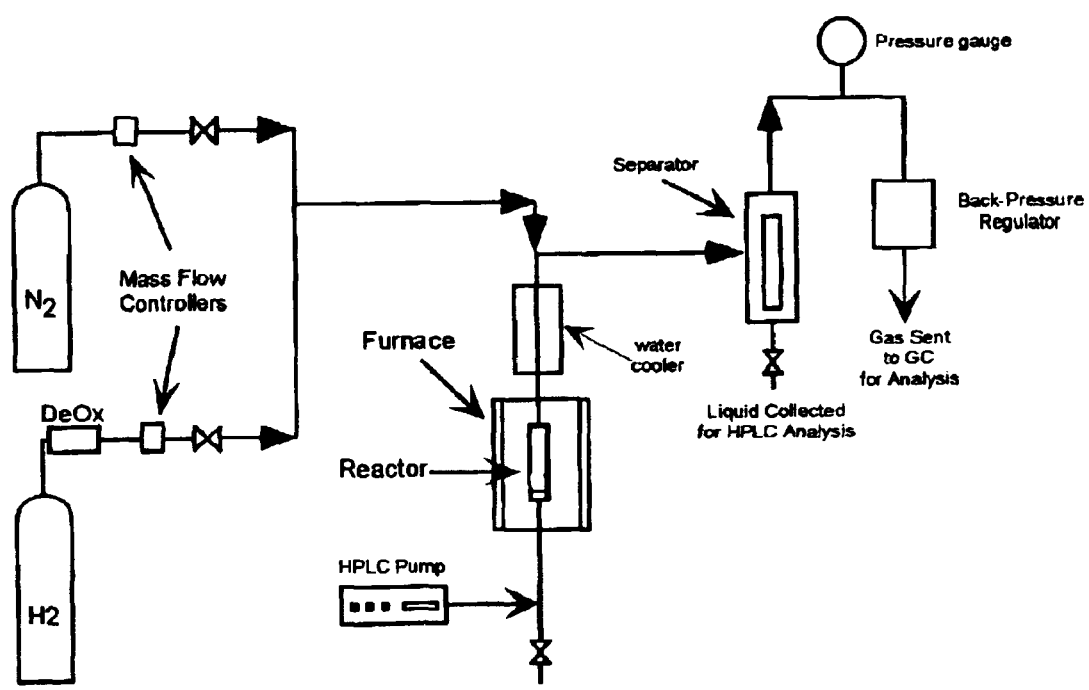
FIG. 3 is a schematic diagram of a reactor system that can be used to carry out the condensed liquid phase reforming of oxygenated hydrocarbons.

Reactor System:

An illustrative reactor system for carrying out the presently claimed method is depicted schematically in FIG. 3. Note that FIG. 3 depicts an exemplary system. Many other reactor configurations could be utilized with equal success.

As shown in FIG. 3, a reactor is disposed within a furnace. Liquid reactants are introduced into the reactor via a pump. As shown in the figure, the pump 16 is a small-scale HPLC pump. (FIG. 3 depicts the prototype reactor that was used to conduct the experiments described in Examples.) Obviously, for full-scale hydrocarbon production, a much larger system, including industrial-scale components, would be utilized.

A nitrogen supply is provided to maintain the overall pressure of the system. Mass flow controllers are provided to regulate the introduction of nitrogen and hydrogen into the system.

A heat exchanger is provided to reduce the temperature of the products exiting the reactor. As shown in FIG. 3, the heat exchanger is a water cooler, but any type of heat exchanger will suffice. The products are then swept into a separator. The design of the separator is not critical to the function of the invention, so long as it functions to separate gaseous products from liquid products. Many suitable separators to accomplish this function are known in the art, including distillation columns, packed columns, selectively-permeable membranes, and the like. A pressure regulator and a back-pressure regulator serve to monitor and maintain the pressure of the system within the set value or range.

In a typical condensed liquid phase reforming reaction according to the present invention, a suitable metal-containing catalyst is placed into the reactor. The metal-containing catalyst is then reduced by flowing hydrogen (from the hydrogen supply) into the reactor at a temperature of roughly 498 K. The pressure of the system is then increased using nitrogen (from the nitrogen supply) to be above the vapor-pressure of water at the given reaction temperature. The pump is then used to fill the reactor with an aqueous solution of reactant oxygenated hydrocarbon (for example, sorbitol, sucrose, lactose, etc.).

The liquid effluent from the reactor is then cooled in the heat exchanger (the water cooler in FIG. 3) and combined with nitrogen flowing at the top of the separator. The gas/liquid effluent is then separated within the separator. The product gas stream can then be analyzed by any number of means, with gas chromatography being perhaps the most easily implemented in-line analysis. Likewise, the effluent liquid may also be drained and analyzed.

The liquid-phase reforming method of the present invention therefore generally comprises loading a metallic catalyst into a reactor and reducing the metal (if necessary). An aqueous solution of the oxygenated hydrocarbon is then introduced into the reactor and the solution is reformed in the presence of the catalyst. The pressure within the reactor is kept sufficiently high to maintain the water and oxygenated hydrocarbon in the condensed liquid phase at the selected temperature.

Oxygenated Hydrocarbons:

Oxygenated hydrocarbons that can be used in the present invention are those that are water-soluble and have at least two carbons. Preferably, the oxygenated hydrocarbon has from 2 to 12 carbon atoms, and more preferably still from 2 to 6 carbon atoms. Regardless of the number of carbon atoms in the oxygenated hydrocarbon, it is much preferred that the hydrocarbon has a carbon-to-oxygen ratio of 1:1.

Preferably, the oxygenated hydrocarbon is a water-soluble oxygenated hydrocarbon selected from the group consisting of ethanediol, ethanedione, glycerol, glyceraldehyde, aldotetroses, aldopentoses, aldohexoses, ketotetroses, ketopentoses, ketohexoses, and alditols. From among the 6-carbon oxygenated hydrocarbons, aldohexoses and corresponding alditols are preferred, glucose and sorbitol being the most preferred. Xylose and xylitol are the preferred oxygenated compounds having 6 carbon atoms. Sucrose is the preferred oxygenated hydrocarbon having more than 6 carbon atoms.

Vapor-phase reforming requires that the oxygenated hydrocarbon reactants have a sufficiently high vapor pressure at the reaction temperature so that the reactants are in the vapor phase. In particular, the oxygenated hydrocarbon compounds preferred for use in the vapor phase method of the present invention include, but are not limited to, ethanediol, glycerol, and glyceraldehyde. When the reaction is to take place in the liquid phase, glucose and sorbitol are the most preferred oxygenated hydrocarbons. Sucrose is also a preferred feedstock for use in the liquid phase.

In the methods of the present invention, the oxygenated hydrocarbon compound is combined with water to create an aqueous solution. The water-to-carbon ratio in the solution is preferably from about 2:1 to about 20:1. This range is only the preferred range. Water-to-carbon ratios outside this range are included within the scope of this invention.

It is much preferred that the water and the oxygenated hydrocarbon are reacted at a pH of from about 1.0 to about 10.0.

Catalysts:

The metallic catalyst systems preferred for use in the present invention comprise one or more Group VIII transitional metals, alloys thereof, and mixtures thereof, preferably (although not necessarily) adhered to a support. From among these metals, the most preferred are nickel, palladium, platinum, ruthenium, rhodium, iridium, cobalt, iron, osmium, alloys thereof, and mixtures thereof. Platinum, ruthenium, nickel, and rhodium are the most preferred.

The Group VIII transition metal catalyst may optionally be alloyed or admixed with a metal selected from the group consisting of Group IB metals, Group IIB metals, and Group VI, and Group VIIb metals. The amount of these added metals should not exceed about 30% of the weight of the Group VIII transition metal catalyst present. The preferred optional metals for inclusion in the catalyst are tin, molybdenum, manganese, chromium, zinc, and rhenium, alloys thereof, and mixtures thereof If loaded onto a support, the metallic catalyst should be present in an amount of from about 0.25% to about 50% by total weight of the catalyst system (the weight of the support being included), with an amount of from about 1% to 30% by total weight being preferred.

If a support is omitted, the metallic catalyst should be in a very finely powdered state, sintered, or in the form of a metallic foam. Where a support is omitted, metal foams are preferred. Metal foams are extremely porous, metallic structures that are reasonably stiff (they are sold in sheets or blocks). They are very much akin in structure to open-cell foamed polyurethane. Gas passing through a metal foam is forced through an extremely tortuous path, thus ensuring maximum contact of the reactants with the metal catalyst. Metal foams can be purchased commercially from a number of national and international suppliers, including Recemat International B.V. (Krimpen aan den Ijssel, the Netherlands), a company that markets "RECEMAT"-brand metal foam. In the United States, a very wide variety of metal foams can be obtained from Reade Advanced Materials (Providence, R.I. and Reno, Nev.).

It is preferred, however, that a support be used. The support should be one that provides a stable platform for the chosen catalyst and the reaction conditions. The supports include, but are not limited to, silica, alumina, zirconia, titania, ceria, carbon, silica-alumina, silica nitride, boron nitride, vanadia, heteropolyacids, and mixtures thereof Furthermore, nanoporous supports such as zeolites, carbon nanotubes, or carbon fullerene may be utilized. From among these supports, silica is preferred.

The support may also be treated, as by surface-modification, to modify surface moieties such hydrogen and hydroxyl. Surface hydrogen and hydroxyl groups can cause local pH variations that would affect catalytic efficiency. The support can be modified, for example, by treating it with a modifier selected from the group consisting sulfates, phosphates, tungstenates, and silanes. Particularly useful catalyst systems for the practice of the invention include, but are not limited to: platinum supported on silica, platinum supported on silica-alumina, platinum supported on alumina, nickel supported on silica-alumina, nickel supported on alumina, ruthenium supported on silica-alumina, ruthenium supported on alumina, palladium supported on silica-alumina, and nickel-platinum supported on silica-alumina. Preferably, the catalyst system is platinum on silica or silica-alumina, with the platinum being further alloyed or admixed with nickel or ruthenium.

The catalyst systems of the present invention can be prepared by conventional methods known to those in the art. These methods include evaporative impregnation techniques, incipient wetting techniques, chemical vapor deposition, wash-coating, magnetron sputtering techniques, and the like. The method chosen to fabricate the catalyst is not particularly critical to the function of the invention, with the proviso that different catalysts will yield different results, depending upon considerations such as overall surface area, porosity, etc.

The liquid phase reforming method of the present invention should generally be carried out at a temperature at which the thermodynamics of the proposed reaction are favorable. The pressure selected for the reactions varies with the temperature. For condensed phase liquid reactions, the pressure within the reactor must be sufficient to maintain the reactants in the condensed liquid phase.

The vapor phase reforming method of the present invention should be carried out at a temperature where the vapor pressure of the oxygenated hydrocarbon compound is at least about 0.1 atm (and preferably a good deal higher), and the thermodynamics of the reaction are favorable. This temperature will vary depending upon the specific oxygenated hydrocarbon compound used, but is generally in the range of from about 100° C. to about 450° C. for reactions taking place in the vapor phase, and more preferably from about 100° C. to about 300° C. for vapor phase reactions. For reactions taking place in the condensed liquid phase, the preferred reaction temperature should not exceed about 400° C.

The condensed liquid phase method of the present invention may also optionally be performed using a salt modifier that increases the activity and/or stability of the catalyst system. Preferably, the modifier is a water-soluble acid. It is preferred that the water-soluble acid is selected from the group consisting of nitrate, phosphate, sulfate, and chloride salts, and mixtures thereof. If an optional modifier is used, it is preferred that it be present in an amount sufficient to lower the pH of the aqueous feed stream to a value between about pH 1 and about pH 4. Generally, the modifier is added in an amount ranging from about 0.5% to about 10% by weight as compared to the total weight of the catalyst system used, although amounts outside this range are included within the present invention.

EXAMPLES

The following Examples are included solely to provide a more complete disclosure of the subject invention. Thus, the following Examples serve to illuminate the nature of the invention, but do not limit the scope of the invention disclosed and claimed herein in any fashion.

In all of the Examples, off-gas streams were analyzed with several different gas chromatographs (GCs), including a Carle GC with a "Porapak Q"-brand column (Waters Corp., Milford, Mass.) to determine hydrogen concentrations, an HP 5890 GC with a thermal conductivity detector and a "Porapak N"-brand column (Waters) to determine carbon monoxide, carbon dioxide, methane, and ethane concentrations, and the HP 5890 GC with a thermal conductivity detector and a "Hayesep D"-brand column (Hayes Separation Inc., Bandera, Tex.) to determine methane, ethane, propane, butane, pentane, and hexane concentrations. Total hydrocarbon and other volatile oxygenates were determined using an HP 6890 GC with a flame ionization detector and an "Innowax"-brand capillary column from Agilent Technologies, Palo Alto, Calif.

EXAMPLE 1

A 5 wt % silica-supported platinum catalyst system (Pt/$SiO_2$) was prepared through the exchange of $Pt(NH_3)_4^{2+}$ with $H^+$ on the silica surface. The preparation procedure involved the following steps: (1) Cab-O-Sil EH-5 was exchanged with an aqueous $Pt(NH_3)_4(NO_3)_2$ solution (Aldrich Chemical, Milwaukee, Wis.) with the degree of exchange controlled by adjusting the pH of the silica slurry with an aqueous, basic solution of $Pt(NH_3)_4(OH)_2$; (2) the resulting material was filtered and washed with deionized water; and (3) and the filtered material was dried overnight in air at 390 K.

EXAMPLE 2

A 5 wt % silica-supported platinum catalyst system was made according to the procedure described in Example 1. The catalyst was, however, modified by dehydroxylation and capping with trimethylethoxysilane. The catalyst system was prepared as follows: (1) fumed silica (Cab-O-Sil, EH-5 grade) was dried at 600 K for 10 hours under flowing helium; (2) platinum was added to the support by vapor-phase deposition of Pt(II) acetylacetonate at 500 K; (3) the resulting $Pt/SiO_2$ catalyst system was calcined at 600 K in flowing oxygen; (4) the calcined catalyst system was reduced at 600 K with flowing hydrogen; (5) the resulting catalyst system was dehydroxylated under flowing helium at 1173 K; (6) the catalyst system was treated with CO at 300 K to prevent the platinum sites from reacting with trimethylethoxysilane; (7) the resulting catalyst was dosed with 4.5 mmol trimethylethoxysilane (Gelest, Inc., Tullytown, Pa.) at 300 K; (8) the catalyst was dosed with CO until the residual pressure was 10 torr; (9) trimethylethoxysilane was dosed onto the catalyst at 473 K; and (10) the resulting catalyst system was calcined with flowing oxygen at 373 K. The catalyst system contained 70 $\mu$mol/g of surface platinum as determined by dosing with carbon monoxide at 300 K.

EXAMPLE 3

Liquid phase reforming of sorbitol was performed using the metallic catalyst systems described in Examples 1 and 2. The apparatus used for the reforming is the apparatus depicted schematically in FIG. 3. The catalyst was loaded into a ¼ inch stainless steel reactor. The catalyst was reduced by flowing hydrogen across the catalyst at a temperature of 225° C. After reduction, the reactor was cooled. The system was then purged with nitrogen, and a HPLC pump was used to fill the reactor with a 10 wt % sorbitol aqueous solution. Once liquid was observed in the separator, the pressure of the system was increased to 21.7 bar with nitrogen (the pressure is controlled by the backpressure regulator 26; see FIG. 3). While the liquid feed was pumped over the catalyst bed, the furnace heated the bed to 225° C. The liquid exited the reactor and was cooled in a double-pipe water cooler (FIG. 3, reference number 22). The fluid from this cooler was combined with the nitrogen flow at the top of the cooler and the gas and liquid were separated in the separator 24.

The liquid was drained periodically for analysis, and the vapor stream passed through the back-pressure regulator 26. This off-gas stream was analyzed with several different GCs to determine the hydrogen concentration, the carbon monoxide, carbon dioxide, methane, and ethane concentrations, and the methane, ethane, propane, butane, pentane, and hexane concentrations. Total hydrocarbon and other volatile oxygenates were also determined by GC.

Figure 4:
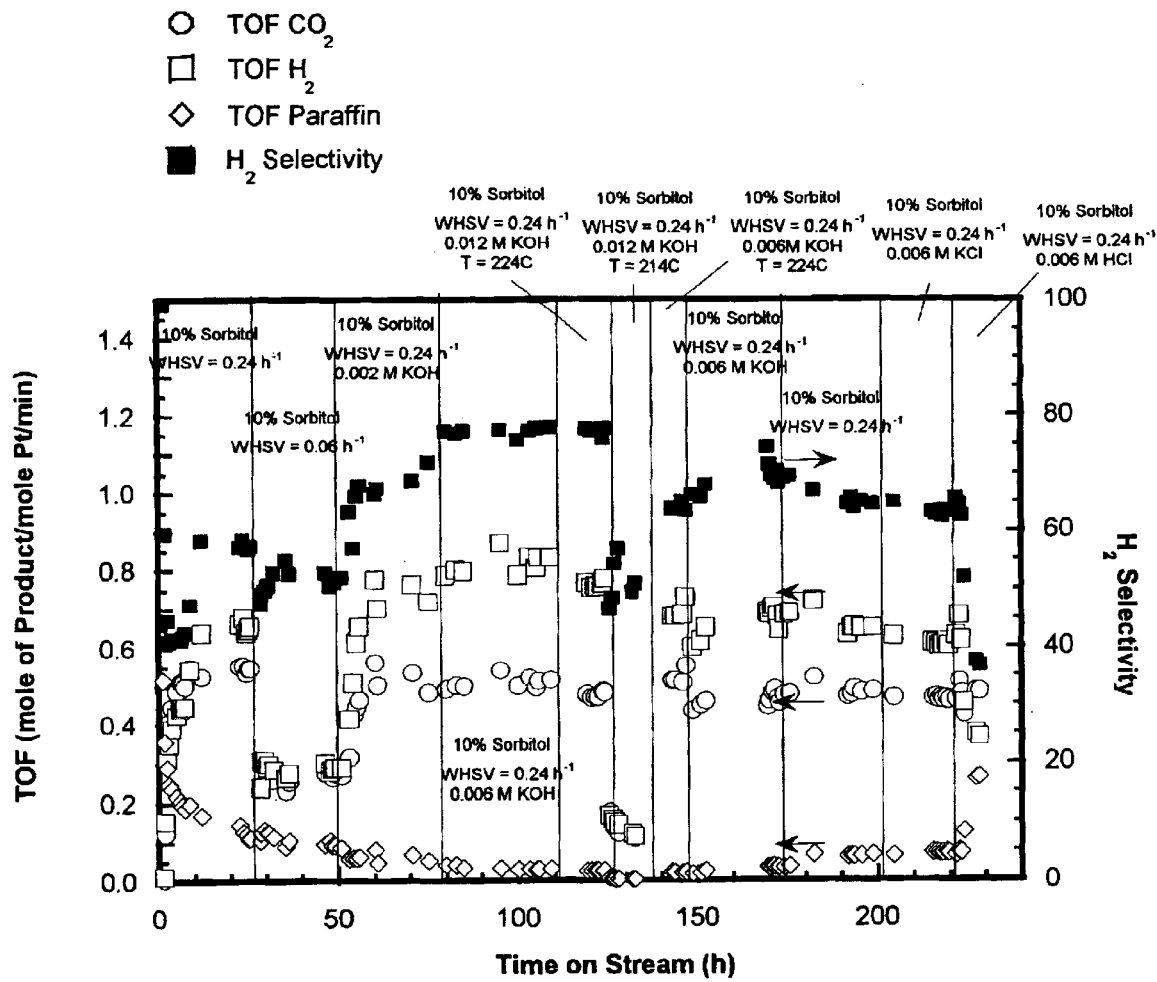
FIG. 4 shows the condensed liquid-phase reforming of a 10 wt % sorbitiol solution over a modified 5 wt % $Pt/SiO_2$ catalyst system. See Example 3.

FIG. 4 shows the result for the liquid-phase conversion of a 10 wt % sorbitol solution at 225° C. over the 5 wt % $Pt/SiO_2$ catalyst that was defunctionalized by capping (see Example 2). This figure shows the observed turnover frequencies (moles of product per mole of surface platinum per minute) for $CO_2$, $H_2$, and carbon found in paraffins. Additionally, this figure shows the $H_2$ selectivity which is defined as the observed hydrogen production divided by the hydrogen produced from the production of the observed $CO_2$ (13/6 $H_2$ per $CO_2$ observed). FIG. 4 shows that supporting platinum on the modified silica enhanced both the rates of production of $CO_2$ and $H_2$, as well as the $H_2$ selectivity. Importantly, this figure also shows that when KOH was added to the 10 wt % sorbitol solution, the rates of $H_2$ production increased and the rate of paraffin production decreased. Additionally, the $H_2$ selectivity increased with the addition of KOH in the liquid feed. Importantly, as the KOH concentration is increased from 0 M KOH to 0.006 M KOH, the $H_2$ selectivity increased from 57% to 77%. In addition, the rate of $H_2$ production increased from 0.65 $min^{-1}$ to 0.83 $min^{-1}$. This example clearly demonstrates that the condensed liquid phase reforming of both glucose and sorbitol is possible.

FIG. 4 shows the result for the liquid-phase conversion of a 10 wt % sorbitol solution at 224° C. and 21.7 bar over the 5 wt % $Pt/SiO_2$ catalyst that was defunctionalized by capping (see Example 2). This figure shows the observed turnover frequencies (moles of product per mole of surface platinum per minute) for $CO_2$, $H_2$, and carbon found in paraffins. This graph illustrates the results obtained when KOH, KCl, or HCl is added to the reaction mixture. All reactions were carried out at a WHSV of 0.24 $h^{-1}$. Note, for example, that $H_2$ selectivity can be decreased by reducing the reaction temperature to 214° C. and adding 0.012 KOH to the reaction. Note also, in the far-right-hand entry of the graph, that the production of paraffins can be increased by adding 0.006 M HCl to the reaction mixture. In this same column, note that $H_2$ selectivity is reduced due to the hydrogen in the system reacting with sorbitol to form paraffins.

EXAMPLE 4

Figure 5:
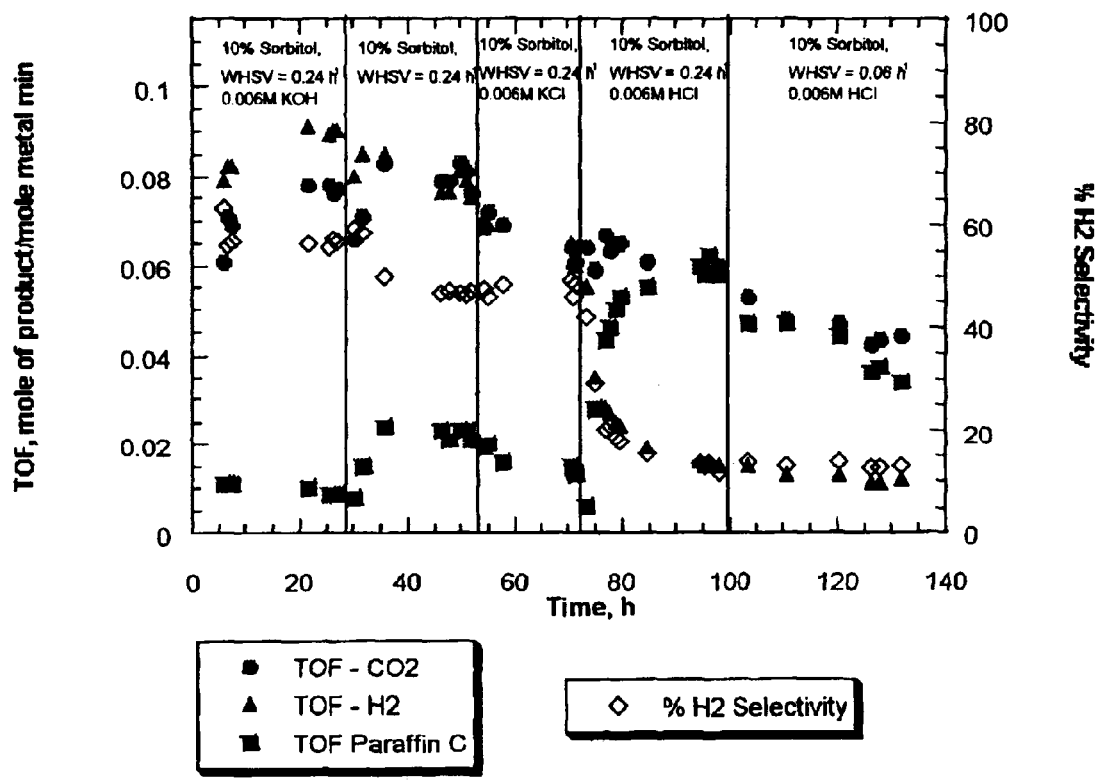
FIG. 5 shows the condensed liquid-phase reforming of a 10 wt % sorbitol solution over a 5 wt % $Pt/SiO_2$ catalyst system. The $SiO_2$ was modified by the addition of potassium. See Example 4.

FIG. 5 depicts the results of a similar series of reactions of a 10% sorbitol solution in water. Here, however, the catalyst was platinum deposited on a potassium-modified silica substrate. The reactions were run in the absence of any added acid or base, or in the presence of added KOH, KCl, or HCl. As can be seen from FIG. 4, adding 0.006 M HCl to the reaction, and feeding the reactants at 0.24 $h^{-1}$ WHSV, paraffin production (■) was greatly increased. Conversely, hydrogen production (▲) was maximized by added 0.006 KOH. This Example shows that the selectivity of the process can be optimized either to yield predominately hydrogen or predominately hydrocarbons, the choice being at the user's discretion and desire.

Figure 6:
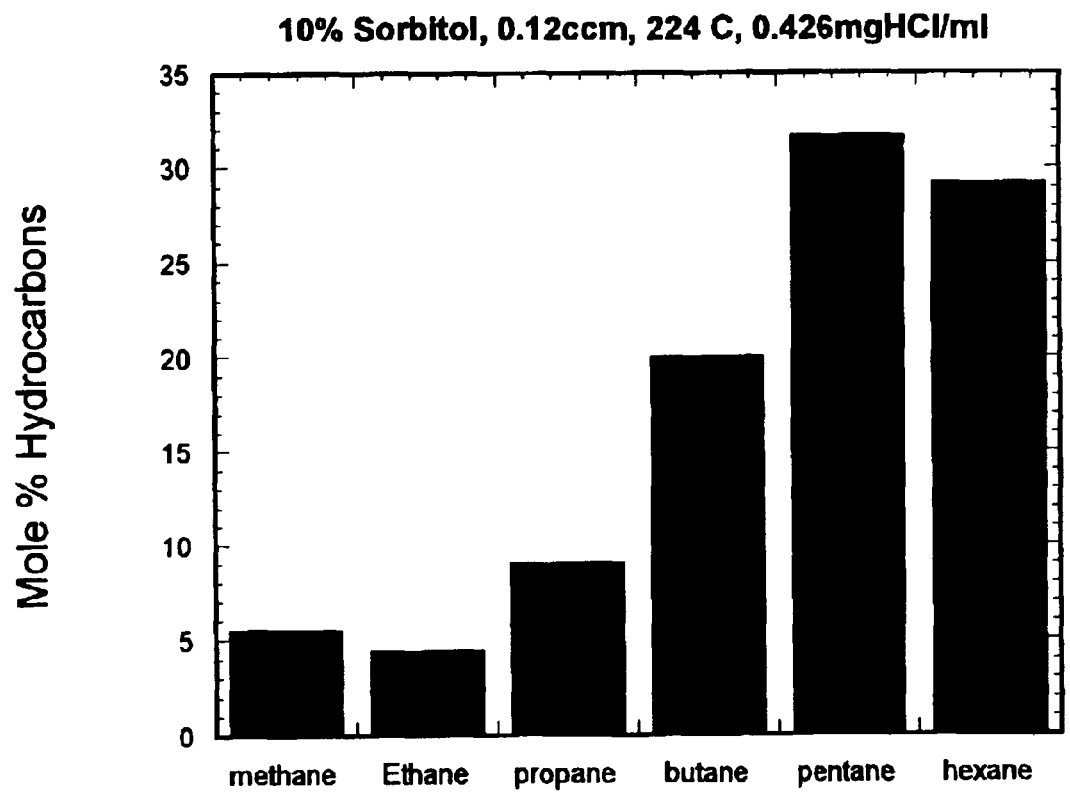
FIG. 6 shows the distribution of hydrocarbon formed for the reaction of sorbitol over 5 wt % Pt on potassium-modified silica. The 10 wt % sorbitol aqueous solution was modified by the addition of HCl. See Example 4.

FIG. 6 is a bar graph showing the product mix (by mole % hydrocarbon) of a reaction according to the present method. Here, the reaction used 10% sorbitol, reacted at 224° C. and 22 bar over the 5 wt % $Pt/SiO_2$ catalyst that was defunctionalized by capping (see Example 11), and in the presence of 0.012 M HCl (i.e., 0.426 mg HCl/ml). As can be seen from FIG. 5, under these reaction conditions, the product mixture is heavily biased toward hydrocarbons having 4, 5, and 6 carbons atoms (i.e., butane, pentane, and hexane). This Example illustrates that not only can the present invention be optimized to maximize the production of hydrogen as compared to hydrocarbons (and vice-versa), but can also be optimized to yield hydrocarbons having a particular range of molecular weights.

EXAMPLE 5

A 3 wt % Pt catalyst supported on silica-alumina (25% alumina) was prepared using the incipient wetting technique to add platinum to the support. The preparation procedure involved the following steps: (1) the support was dried at 120° C.; (2) platinum was added to the silica-alumina by adding dropwise an aqueous solution of the tetramine platinum nitrate (Aldrich) (approximately 1.5 gram of solution per gram of catalyst); (3) the impregnated catalyst was dried at 120° C. overnight; (4) the dried catalyst was treated in a flowing 10 mol % $O_2$ in helium stream at 260° C. for 2 h; and (5) the catalyst was cooled to room temperature and stored until testing.

EXAMPLE 6

The 3 wt % $Pt/SiO_2$—$Al_2O_3$ prepared in Example 5 was first reduced in a stainless-steel tubular reactor under flowing hydrogen at 260° C., and the total pressure of the system was increased by addition of nitrogen to a value slightly higher than the vapor pressure of water that is produced at the reaction temperature. An aqueous solution containing sorbitiol was then fed continuously (using a HPLC pump) to the reactor heated to the desired reaction temperature. The liquid/gas effluent from the reactor was combined with a nitrogen carrier-gas flow at the top of the reactor, and the gas and liquid were separated in a separator. The effluent liquid was drained periodically for analysis, and the gas stream was analyzed with several gas chromatographs (GC). FIG. 6 shows the conversion of sorbitol, selectivity to hydrocarbons (defined as moles of carbon in outlet hydrocarbons divided by moles of carbon in sorbitol reacted), and hydrogen selectivity (defined as moles $H_2$ observed, divided by 13 moles of $H_2$ moles theoretically produced per mole of sorbitol reacted). Both the hydrocarbon and hydrogen selectivities are percentages.

Figure 7:
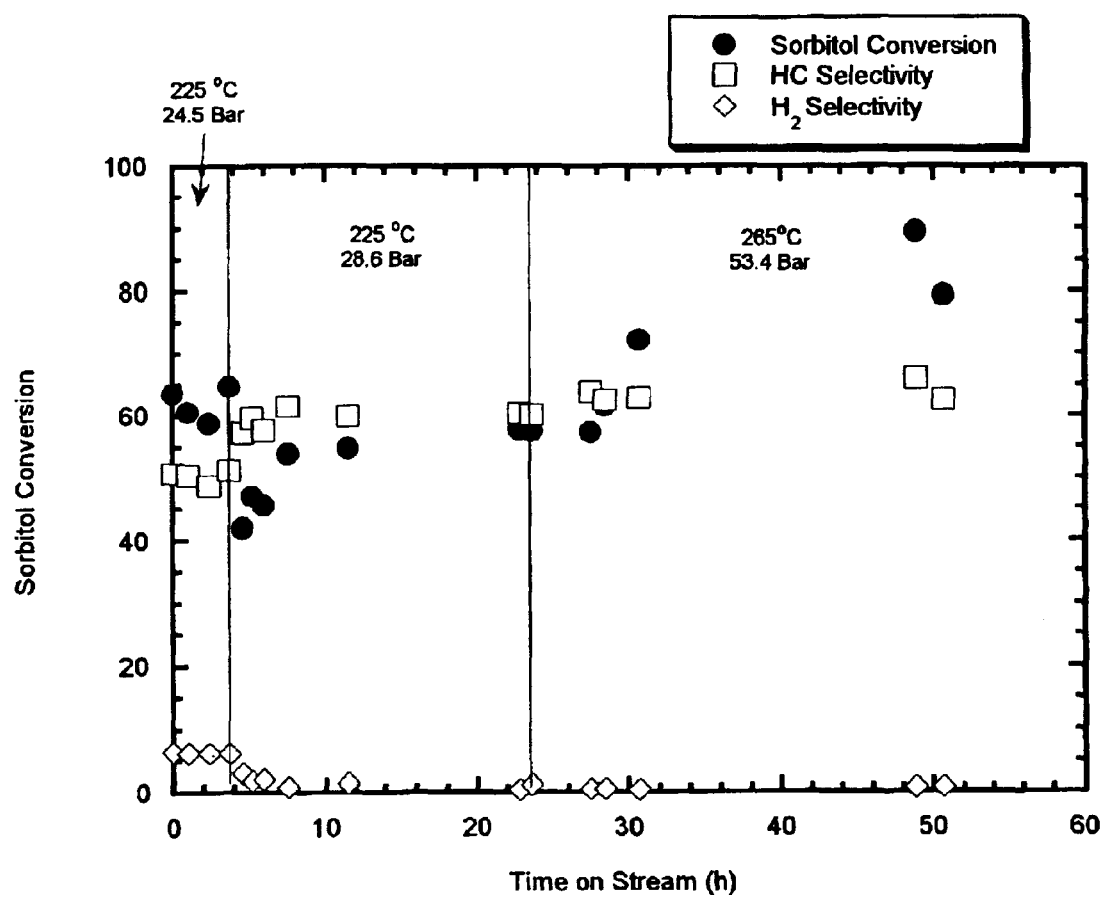
FIG. 7 shows the condensed liquid-phase reforming of a 5 wt % sorbitol solution over a 3 wt % $Pt/SiO_2—Al_2O_3$ catalyst system. See Example 6.

FIG. 7 shows that sorbitol conversion of over 50% was observed at 225° C. and the selectivity to hydrocarbons was increased when the pressure was increased from 24.5 bar to 28.6 bar. When the temperature was increased to 265° C., the sorbitol conversion increased to nearly 80%, with hydrocarbon selectivities of nearly 65%.

Figure 8:
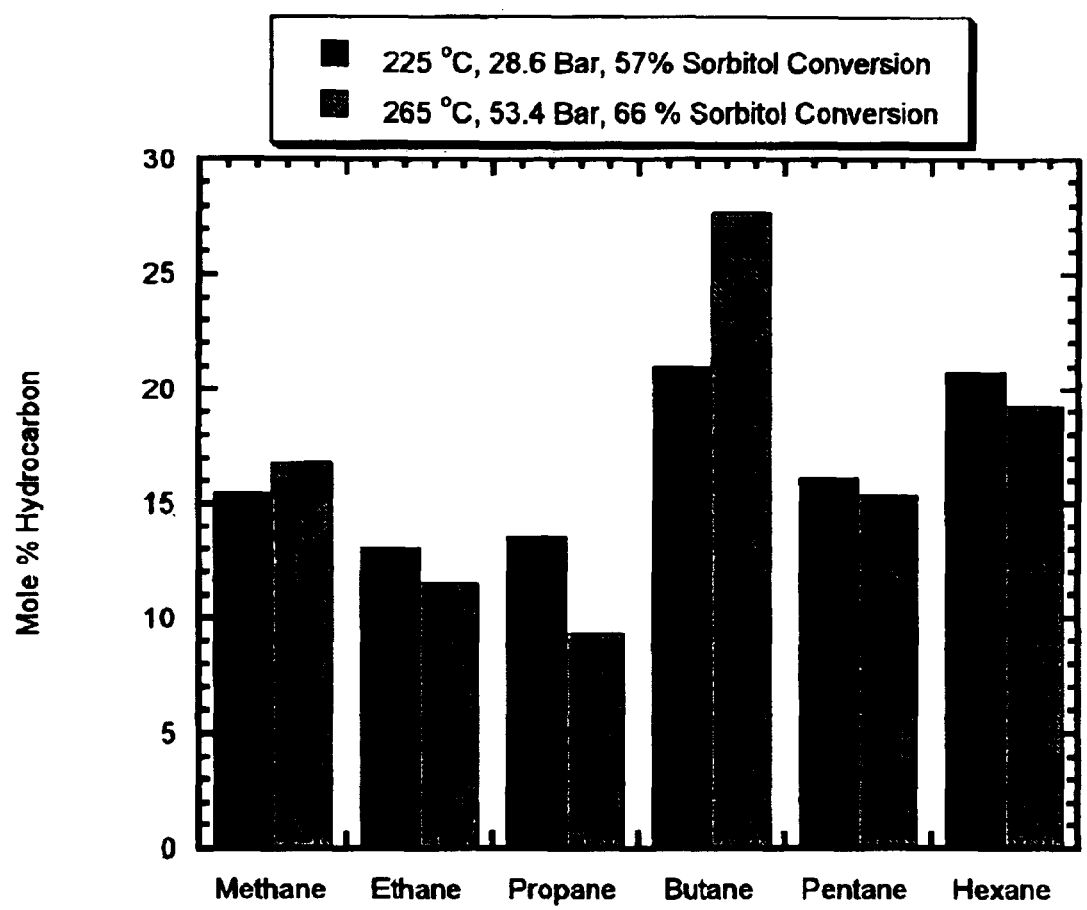
FIG. 8 shows the distribution of hydrocarbon formed for the reaction of a 5 wt % sorbitol solution over a 3 wt % $Pt/SiO_2—Al_2O_3$ catalyst system. See Example 6.

FIG. 8 is a bar graph showing the product mix (by mole % hydrocarbon) of a reaction according to the present method. Here, the reaction used 5% sorbitol, reacted at 224° C. and 28.6 bar and at 265° C. and 53.4 bar over the 3 wt % $Pt/SiO_2$—$Al_2O_3$ catalyst. As can be seen from FIG. 8, under these reaction conditions, the product mixture is biased toward hydrocarbons having 4, 5, and 6 carbons atoms (i.e., butane, pentane, and hexane). This Example illustrates that a acidic support is desirable to maximize the production of hydrocarbons.

The significance of all of the Examples given above is that they demonstrate that the vapor-phase and condensed liquid-phase reformation of oxygenated hydrocarbons to yield hydrogen and hydrocarbons is possible using a host of different types of Group VIII metal-containing catalysts.

EXAMPLE 7

The catalyst of Example 2 was utilized to process a 10% aqueous-glucose solution at 218° C. At a weight hourly space velocity of 0.36 grams of glucose per gram of catalyst per h, nearly 50% of the glucose was converted to fuel gas. The composition of this fuel gas was analyzed and shown to be 62.3 mol % $CO_2$, 19.5 mol % $H_2$, 2.1 mole % $CH_4$, 1.0 mol % $C_2H_6$, 11.3 mol % $C_3H_8$, 2.3 mol % $C_4H_{10}$, 0.9 mol % $C_5H_{12}$, 0.6 mol % $C_6H_{14}$, and 600 ppm CO.

EXAMPLE 8

A catalyst was prepared by first adding 14 wt % tungsten oxide to zirconia. The resulting mixed oxide was calcined at 500° C. and then impregnated with tetramine platinum nitrate using the incipient wetting technique. The resulting catalyst was dried at 120° C.; the dried catalyst was treated in a flowing 10 mol % $O_2$ in helium stream at 260° C. for 2 h; and the catalyst was cooled to room temperature and stored until testing.

EXAMPLE 9

The catalyst of Example 8 was utilized to process a 10% aqueous-sorbitol solution at 225° C. The catalyst was first reduced in a stainless-steel tubular reactor under flowing hydrogen at 260° C., and the total pressure of the system was increased by addition of nitrogen to 30 bar. At a weight hourly space velocity of 0.10 grams of glucose per gram of catalyst per h, nearly 46% of the sorbitol was converted to fuel gas. The composition of this fuel gas was analyzed and determined to be 64.7 mol % $CO_2$, 6.2 mol % $H_2$, 11.4 mole % $CH_4$, 3.8 mol % $C_2H_6$, 3.3 mol % $C_3H_8$, 3.7 mol % $C_4H_{10}$, 3.3 mol % $C_5H_{12}$, and 3.8 mol % $C_6H_{14}$.

What is claimed is:

1. A method of producing hydrocarbons comprising: reacting water and a water-soluble oxygenated hydrocarbon having at least two carbon atoms, in the presence of a metal-containing catalyst, wherein the catalyst comprises a metal selected from the group consisting of Group VIIIB transitional metals, alloys thereof, and mixtures thereof, wherein hydrocarbons are produced.

2. The method of claim 1, wherein the water and the oxygenated hydrocarbon are reacted at a temperature of from about 100° C. to about 450° C., and at a pressure where the water and the oxygenated hydrocarbon are gaseous.

3. The method of claim 1, wherein the water and the oxygenated hydrocarbon are reacted at a temperature of from about 100° C. to about 300° C., and at a pressure where the water and the oxygenated hydrocarbon are gaseous.

4. The method of claim 1, wherein the water and the oxygenated hydrocarbon are reacted at a temperature not greater than about 400° C., at a pressure where the water and the oxygenated hydrocarbon remain condensed liquids.

5. The method of claim 1, wherein the water and the oxygenated hydrocarbon are reacted at a pH of from about 1.0 to about 10.0.

6. The method of claim 1, wherein the catalyst comprises a metal selected from the group consisting of nickel, palladium, platinum, ruthenium, rhodium, iridium, cobalt, iron, osmium, alloys thereof, and mixtures thereof.

7. The method of claim 1, wherein the catalyst is further alloyed or mixed with a metal selected from the group consisting of Group IB metals, Group IIB metals, Group VIb, and Group VIIb metals.

8. The method of claim 1, wherein the catalyst is further alloyed or mixed with a metal selected from the group consisting of copper, tin, manganese, chromium, molybdenum, zinc, and rhenium.

9. The method of claim 1, wherein the catalyst is adhered to a support.

10. The method of claim 9, wherein the support is selected from the group consisting of silica, alumina, zirconia, titania, vanadia, ceria, carbon, silica-alumina, silica nitride, boron nitride, heteropolyacids, and mixtures thereof.

11. The method of claim 9, wherein the support is surface-modified to create Brønsted acid sites thereon, whereby acidity of the support is increased.

12. The method of claim 9, wherein the support is modified by treating it with a modifier selected from the group consisting of silanes, sulfates, phosphates, tungstenates, oxides of molybdenum, and combinations thereof.

13. The method of claim 9, wherein the support is silica modified with trimethylethoxysilane.

14. The method of claim 9, wherein the support is a zeolite.

15. The method of claim 9, wherein the support is a carbon nanotube or a carbon fullerene.

16. The method of claim 9, wherein the support is a nanoporous support.

17. The method of claim 1, wherein the water and the oxygenated hydrocarbon are reacted at a pressure less than the vapor pressure of water at the desired reaction temperature.

18. The method of claim 1, wherein the water and the oxygenated hydrocarbon are reacted at a temperature not greater than about 400° C., at a pressure where the water and the oxygenated hydrocarbon remain condensed liquids, and further comprising reacting the water and the water-soluble oxygenated hydrocarbon in the presence of a water-soluble acid.

19. The method of claim 18, wherein the water-soluble acid is selected from the group consisting of a nitrate, phosphate, sulfate, and chloride acid salts, and mixtures thereof.

20. The method of claim 1, wherein the water-soluble oxygenated hydrocarbon has a carbon-to-oxygen ratio of 1:1.

21. The method of claim 1, wherein the water-soluble oxygenated hydrocarbon has from 2 to 12 carbon atoms.

22. The method of claim 1, wherein the water-soluble oxygenated hydrocarbon is selected from the group consisting of ethanediol, ethanedione, glycerol, glyceraldehyde, aldotetroses, aldopentoses, aldohexoses, ketotetroses, ketopentoses, ketohexoses, and alditols.

23. The method of claim 1, wherein the water-soluble oxygenated hydrocarbon is selected from the group consisting of aldohexoses and corresponding alditols.

24. The method of claim 1, wherein the water-soluble oxygenated hydrocarbon is selected from the group consisting of xylose, glucose and sorbitol.

25. The method of claim 1, wherein the water-soluble oxygenated hydrocarbon is a disaccharide.

26. A method of producing $C_1$ to $C_6$ hydrocarbons comprising: reacting water and a water-soluble oxygenated hydrocarbon having at least two carbon atoms, at a temperature not greater than about 400° C., at a pressure where the water and the oxygenated hydrocarbon remain condensed liquids, and in the presence of a metal-containing catalyst, wherein the catalyst comprises a metal selected from the group consisting of Group VIIIB transitional metals, alloys thereof, and mixtures thereof, wherein $C_1$ to $C_6$ hydrocarbons are produced.

27. The method of claim 26, wherein the catalyst comprises a metal selected from the group consisting of nickel, palladium, platinum, ruthenium, rhodium, iridium, cobalt, iron, osmium, alloys thereof, and mixtures thereof.

28. The method of claim 26, wherein the catalyst is further alloyed or mixed with a metal selected from the group consisting of Group IB metals, Group IIB metals, Group VIb, and Group VIIb metals.

29. The method of claim 26, wherein the catalyst is further alloyed or mixed with a metal selected from the group consisting of copper, zinc, tin, manganese, chromium, molybdenum, and rhenium.

30. The method of claim 26, wherein the catalyst is adhered to a support.

31. The method of claim 30, wherein the support is selected from the group consisting of silica, alumina, zirconia, titania, ceria, carbon, silica-alumina, vanadia, heteropolyacids, silica nitride, boron nitride, and mixtures thereof.

32. The method of claim 30, wherein the support is modified by treating it with a modifier selected from the group consisting of sulfates, phosphates, tungstenates, oxides of molybdenum, and silanes.

33. The method of claim 30, wherein the support is silica modified with trimethylethoxysilane.

34. The method of claim 30, wherein the support is a zeolite.

35. The method of claim 30, wherein the support is a carbon nanotube or a carbon fullerene.

36. The method of claim 30, wherein the support is a nanoporous support.

37. The method of claim 26, further comprising reacting the water and the water-soluble oxygenated hydrocarbon in the presence of a water-soluble acid.

38. The method of claim 37, wherein the water-soluble acid is selected from the group consisting of $H_2SO_4$, $HNO_3$, $H_3PO_4$, and HCl.

39. The method of claim 26, wherein the water-soluble oxygenated hydrocarbon has a carbon-to-oxygen ratio of 1:1.

40. The method of claim 26, wherein the water-soluble oxygenated hydrocarbon has from 2 to 12 carbon atoms.

41. The method of claim 26, wherein the water-soluble oxygenated hydrocarbon is selected from the group consisting of ethanediol, ethanedione, glycerol, glyceraldehyde, aldotetroses, aldopentoses, aldohexoses, ketotetroses, ketopentoses, ketohexoses, and alditols.

42. The method of claim 26, wherein the water-soluble oxygenated hydrocarbon is selected from the group consisting of aldohexoses and corresponding alditols.

43. The method of claim 26, wherein the water-soluble oxygenated hydrocarbon is selected from the group consisting of xylose, glucose and sorbitol.

44. The method of claim 26, wherein the water-soluble oxygenated hydrocarbon is a disaccharide.

45. A method of producing $C_1$ to $C_6$ alkanes comprising: reacting water and a water-soluble oxygenated hydrocarbon having at least two carbon atoms, at a temperature of from about 100° C. to about 450° C., and at a pressure where the water and the oxygenated hydrocarbon are condensed liquids, in the presence of a metal-containing catalyst, wherein the catalyst comprises a metal selected from the group consisting of Group VIII transitional metals, alloys thereof, and mixtures thereof, the catalyst being adhered to a support wherein $C_1$ to $C_6$ alkanes are produced.

46. The method of claim 45, wherein the support is selected from the group consisting of silica, alumina, zirconia, titania, ceria, vanadia, heteropolyacids, carbon, silica-alumina, silica nitride, and boron nitride, wherein the support is surface-modified to create Brønsted acid sites thereon, whereby acidity of the support is increased.

47. The method of claim 46, wherein the support wherein the support is modified by treating it with a modifier selected from the group consisting of silanes, sulfates, phosphates, tungstenates, oxides of molybdenum, and combinations thereof.

48. The method of claim 45, wherein the support is silica modified with trimethylethoxysilane.

49. The method of claim 45, wherein the water-soluble oxygenated hydrocarbon has a carbon-to-oxygen ratio of 1:1.

50. The method of claim 45, wherein the water-soluble oxygenated hydrocarbon is selected from the group consisting of ethanediol, ethanedione, glycerol, glyceraldehyde, aldotetroses, aldopentoses, aldohexoses, ketotetroses, ketopentoses, ketohexoses, and alditols.

* * * * *